(12) United States Patent
Doyle

(10) Patent No.: US 6,402,713 B1
(45) Date of Patent: Jun. 11, 2002

(54) KNEE ORTHOSIS AND HINGE JOINT

(76) Inventor: Brian P. Doyle, 60 Clifton Road, Toronto, Ontario (CA), M4T 2E9

( * ) Notice: Subject to any disclaimer, the term of this patent is extended or adjusted under 35 U.S.C. 154(b) by 0 days.

(21) Appl. No.: 09/420,156

(22) Filed: Oct. 18, 1999

(51) Int. Cl.[7] .................................................. A61F 5/00
(52) U.S. Cl. ........................................... 602/26; 602/16
(58) Field of Search ............................... 602/5, 20, 23, 602/16, 26; 623/39

(56) References Cited

U.S. PATENT DOCUMENTS

| | | |
|---|---|---|
| 73,768 A | 1/1868 | Allen |
| 649,237 A * | 5/1900 | Dyson .......................... 602/16 |
| 4,323,059 A | 4/1982 | Rambert et al. |
| 4,699,129 A | 10/1987 | Aaserude et al. |
| 4,854,308 A * | 8/1989 | Drillio ....................... 602/26 X |
| 4,961,416 A | 10/1990 | Moore et al. |
| 5,018,514 A | 5/1991 | Grood et al. |
| 5,042,464 A * | 8/1991 | Skwor et al. .................. 128/80 |
| 5,103,811 A | 4/1992 | Crupi, Jr. |
| 5,458,657 A * | 10/1995 | Rasmusson .................. 623/38 |
| 5,624,389 A * | 4/1997 | Zepf .......................... 602/16 X |
| 5,645,524 A * | 7/1997 | Doyle ........................... 602/16 |

* cited by examiner

*Primary Examiner*—Denise Pothier

(57) ABSTRACT

A knee orthosis for supporting an injured knee or to protect a knee from injury and to aid the knee in rehabilitation while permitting flexion and extension movements of such knee, such movements involving both the displacement of the femur portion of such joint away from the tibia portion and also involving sliding, twisting and tilting movement of such femur portion relative to such tibia portion, the knee support having an upper cuff which can be secured around a portion of a leg, above the knee, a lower cuff which can be secured around the leg below the knee, attachments on the upper and lower cuffs, and, linear bearings secured to the attachments on either side of the knee, and placed to allow movement of one of the cuffs away from the other and enabling free displacement, rotating and sliding movement of the knee joint and a hinge joint device for connecting the upper and lower cuffs.

14 Claims, 6 Drawing Sheets

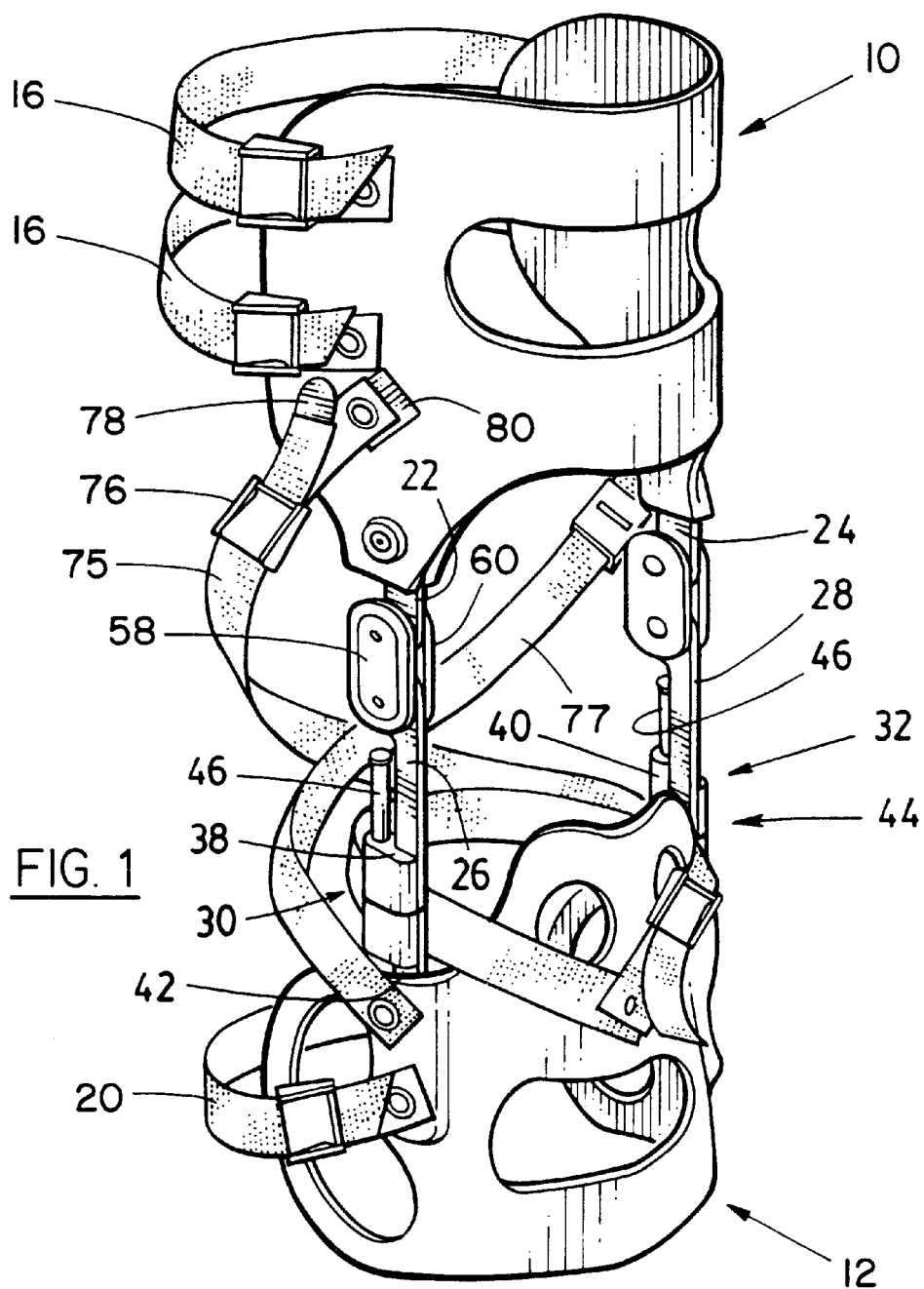

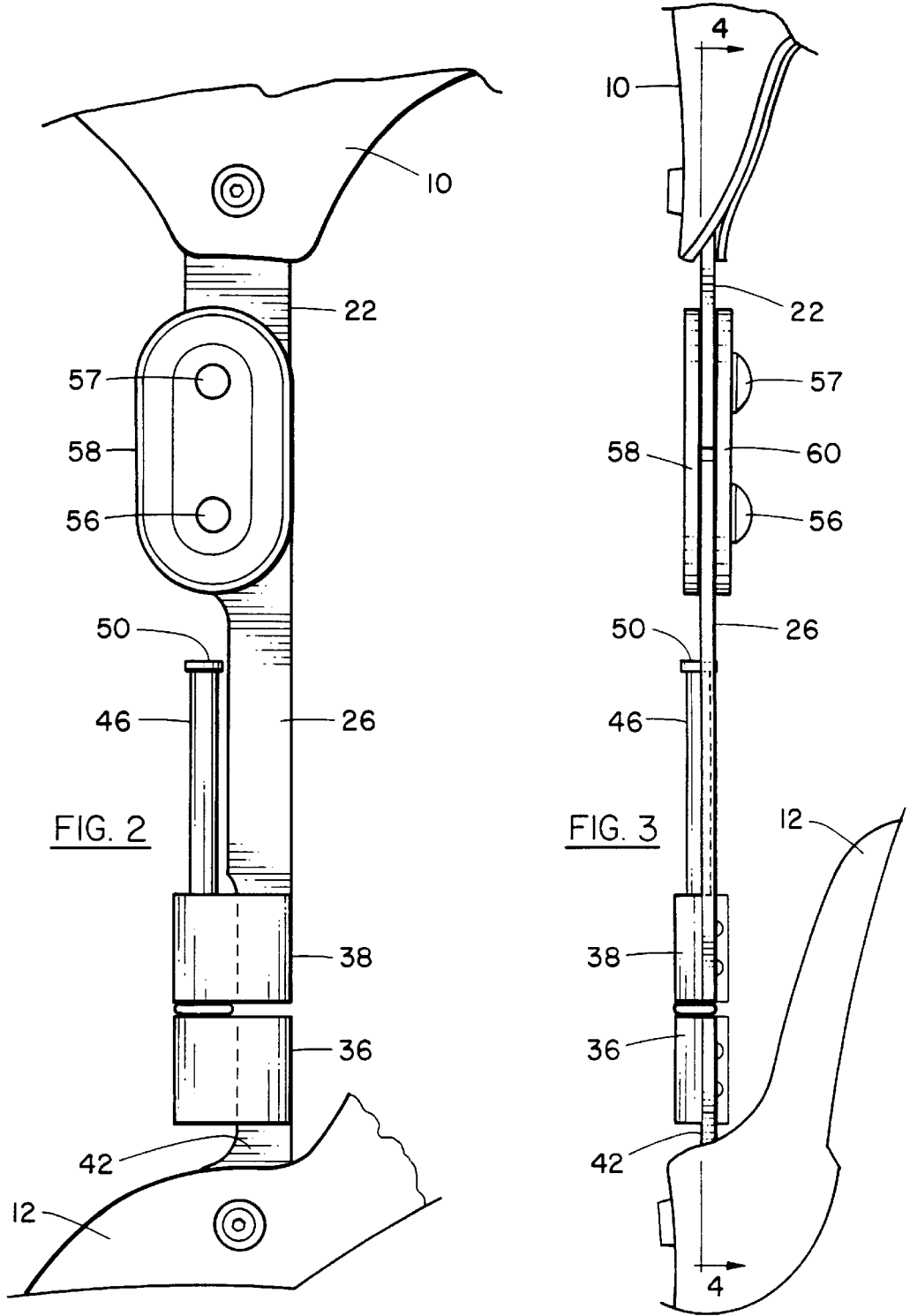

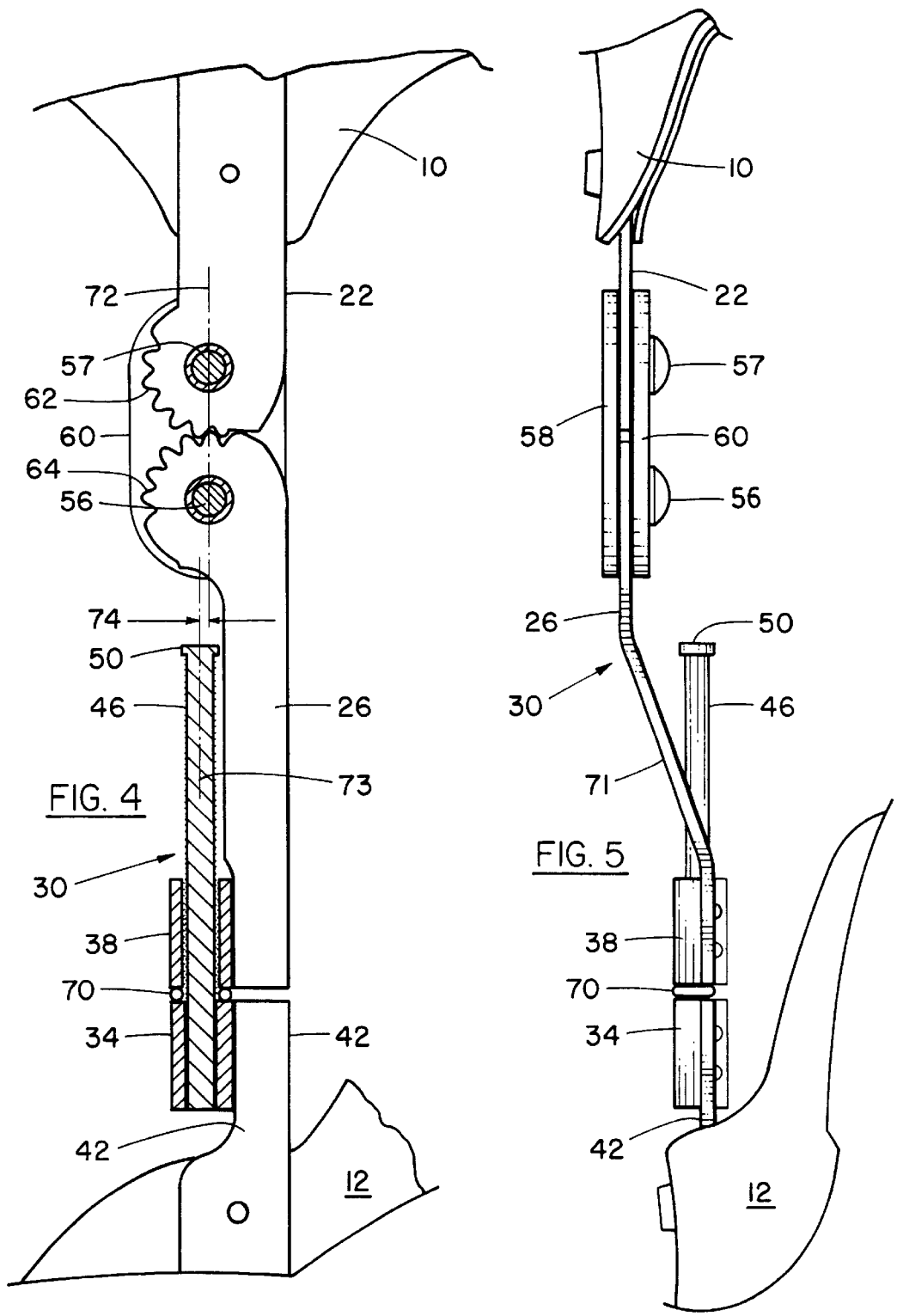

KNEE ORTHOSIS AND HINGE JOINT

BACKGROUND OF THE INVENTION

1. Field of the Invention

The present invention relates to orthosis', and in particular an orthosis designed to provide a structural movable mechanism to support a human knee joint. Such devices are usually known as a knee brace or knee orthosis. Also described is a hinge mechanism for use in such an orthosis.

2. Description of the Prior Art

Injuries to the human knee are common and can be the result of many different occurrences from athletic injuries to the onset of old age. A healthy knee operates to provide forward and backward hinging motion, tilting, rotating, and sliding motion of the upper leg or femur relative to the lower leg or tibia.

The knee joint consists of two principle bony structures, an upper bone, the femur, and a lower bone, the tibia. The femur has two large rounded knuckles of different sizes with the center located rearward of the center line of the vertical component of the bone. The articular surfaces on the knuckles have some of their contact surface facing downwards towards the tibia and a smaller, radiuses surfaces facing the back of the leg. The tibia, on the other hand, has a large relatively flat articular surface, primarily facing upwards towards the femur. When the human knee is straightened to full extension the lower portion of the large rounded knuckle of the femur sits a top the upwards facing articular surface of the tibia.

When the knee is moved by flexing the joint from this straightened position, the femur, while rotating on the rearward portion of the knuckle will also slide forward on the flat downwards facing portion of the articular surface of the femur. While this is occurring the femur may also tilt from side to side during the flexion process.

All of these complex motions, in a healthy knee joint, are controlled by a complexity of ligaments, muscles and tendons. When an injury occurs many of these elements can be torn from their attachment points in the skeletal or musculature, rendering them useless in controlling of the motion of the femur with respect to the tibia. In many cases, as the result of these types of injuries, the knee can no longer flex and extend normally and may in fact, dislocate and re-injure itself.

The basic understanding of the mechanism of these types of injuries are well understood by the medical profession. Numerous attempts have been made to externally and internally replace the torn element with a mechanical apparatus which would act similarly to the torn element. Traditionally this apparatus, which may include orthosis, or even ligamental repair, has resulted in a restriction of overall motion of the joint and may, in many cases, cause re-injury or dislocation of the knee. An orthosis is generally used to attempt to support the knee externally and it would have an upper cuff, wrapped around the upper leg and a lower cuff, wrapped around the lower leg, which would likely be connected together via a linkage. This linkage was usually a simple hinge of some fashion mechanically attached to the upper cuff and directed downwards where it would be fastened to the lower cuff.

It is understood that the knee tilts, slides and pivots during flexion and extension when healthy. It is also apparent that an orthosis for the knee with a simple hinge on the side(s), does not. In practice this means the orthosis restricts all types of movement of the knee preventing the knee from functioning as it should.

When an orthosis, as described above, is placed on an injured knee, the upper and lower cuffs are unable to remain conformal to the leg as the knee is flexed. This results in a scrubbing action between the leg and brace often resulting in skin irritation. Further detrimental effects, as the orthosis separates from the leg as the knee is flexed, the orthosis loses contact with the leg allowing the orthosis to descend down the leg. It is obvious that if the orthosis is sliding down the leg it cannot support the knee and may in fact, create hazards of its own to the knee while being used.

The effects of the knee orthosis restricting the movement of the knee in this fashion, can prevent the wearer of the orthosis from doing even simple things like sifting into a low chair. It is often understood by wearers of the orthotic devices, that if they should try to exercise or participate in athletic endeavours they may be gravely risking re-injury of the joint. In addition to this and because the orthosis cannot slide and tilt the way the knee does, the orthosis creates internal forces in the knee joint further adding to the wearers discomfort.

After considerable effort, the joint motion of the human knee has begun to be understood. Its complex movements can be generally described in the following:

When in full extension, the lower most portion of the femurs articular surfaces are in direct contact with the upward facing plateau surfaces of the tibia. As the knee begins to flex, the femur will begin to slide in a forward direction on the surface of the tibial plateau and as the result of the differences in the femurs knuckle sizes, begin a slight tilting motion. As the knee continues to flex, the larger radius knuckle of the femur begins to rotate on the tibial plateau, and due to the center of rotation of the knuckle being behind the center line of the vertical portion of the femur, this lifts the front of the femur articular surface from contacting the forward most portion of the articular surface of the tibia. While lifting at the front of femur is taking place, and due to the difference in knuckle size of the femur, an external rotation of the femur with respect to the tibia is introduced.

As the knee continues to flex the relative displacements in translation forward, rotation outwards, lifting upwards and tilting sideways, begin to increase. In a standard orthosis, where these motions are not included in the mechanical joint design, these relatively large displacements cause internal pressure on the muscle-skeletal structure due to the restrictive nature of the orthosis. This can, and does, when used on an injured leg where the ligamental structure has been torn away from the bone, force the femur into an abnormal, if not extremely uncomfortable positions. This abnormal motion has been known to accelerate degradation of the articular surfaces of the femur and tibia. During that abnormal displacement of the femur, it is often noted on wearers of standard orthosis, that significant gaping of the upper cuff with respect to the thigh muscle. This generally results in the brace sliding downwards with each step, resulting in the wearer holding the top of the brace to prevent this downward migration. This leaves the knee joint completely unsupported and possibly resulting in further injury.

As is well understood by the medical profession, people come in all different sizes and shapes. The problem often faced by the designers of the knee orthosis, is its suitability to be manufactured. Many orthotic manufacturers have been unable to reach a compromise between manufacturability, adaptability to the many shapes and sizes of people and functionability after the orthosis has been manufactured. An example of this is when two hinges are mounted on either side of the knee connected by an upper and lower cuff.

Contributing to discomfort is the positioning of the strapping system used to hold the orthosis on to the leg. It has been well understood that the Anterior Cruciate Ligament will prevent, when fully attached, the femur from sliding backwards off the tibial plateau. This is most pronounced when the leg is slightly bent and the center line of the femur is directed in a rearward fashion towards the back of the tibial plateau. The problem with the placement of many strapping systems knee orthosis is that they allow the head of the femur to continue in a rearwards motion often to the point of dislocation. An example of this style of dislocation is often seen in skiing when the ski bindings do not release and the skier falls directly forward resulting in a backwards displacement of the femur on the tibia.

It is often noted by medical professionals that individuals who have had injuries to one knee, will, unfortunately suffer an injury to the other knee at some point. The reasons for this are not clearly understood, however they may be based on genetic considerations. The results of this, of course is the need for the individual to wear two knee orthosis at one time. Current knee braces exacerbate the problems described herein when two are used. An example of this is if the individual wearing the braces may in fact catch one brace on the other resulting in a tripping hazard. The conformity of the joints proximal to the side of the knee becomes a clear and present danger to the individual required to wear two braces.

In U.S. Pat. No. 5,645,524, inventor Brian P. Doyle, dated Jul. 8, 1997, there is a device described which has been successful in helping people function normally after an injury as described above. Through much experience, it has been realized that certain people may in fact benefit from additional features and adjustments to the location of the mechanical elements on the orthosis described therein. These features and adjustments provide additional comfort and range of motion suitable to certain types of injuries and can further accelerate the recovery process of the individual wherein the orthosis and these features further the comfort level of the wearer to the point where they are desiring to wear an orthosis to protect an uninjured knee. This allows for the wearer to use orthosis on both knees comfortably. Part of this is achieved by a change in the finish of the mechanical orthosis joints resulting in a change to manufacturing process allowing the mechanical elements of the orthosis to be conformal to the shape of the wearers leg. These changes in manufacturing also reduce the cost and time required to deliver the orthosis to the wearer.

In addition to these changes, control features have been added to orthosis, such as strapping systems which increase the torsional and longitudinal stability of the orthosis. These additions decrease the amount of rehabilitation time required by the wearer while increasing the effects of the rehabilitation program. All of these features work in concert with each other to enhance the range of motion of the wearer while using the orthosis.

Typically, as well understood by the medical profession, there are varying grades of injuries to the ligamental structures within the knee. In assessing the nature of the injury a trained physician can determine if a particular ligament is fully torn from itself, partially torn or simply stretched. In the previous patents there is described in a device wherein a sliding element is located on the outmost side of the hinge element the proximity and location to that element have been found to control the relationship between the femur and the tibia when either the anterior cruciate ligament or the posterior cruciate ligament have been completely separated.

Because this previous design was successful in helping people with complete rupture of the ligaments it became apparent that injuries such as partially torn and merely stretched ligaments could, in fact be encouraged to rejuvenate themselves given the right conditions. As the medical profession knows, immobilizing of a partially torn ligament is often detrimental to the injured knee. In fact the ideal circumstances for recovery of such an injury is to allow the knee complete range of motion and to assure, that at no point the joint can experience abnormal movements. The placement of the sliding elements with relation to the hinge elements of the previous design allows for a greater degree of flexibility, most notably the rotation of the upper cuff to the lower cut at full extension, while still maintaining and preventing abnormal knee movements. This allows the knee with the partial or stretched knee ligaments to be rehabilitated using this orthotic design quickly and effectively.

It has also been noted by the medical profession, that re-injury is often caused by the foot rotating outward unexpectedly and abnormally twisting the knee. Further to the success of the previous design, there was included two straps which when attached on the inner upper cuff and re-attached with an adjustment mechanism on the outside of the lower cuff and complimented by the same on the opposite side of the leg not only prevents the upper femur from displacing abnormally backwards on the tibia but also controls the unnecessary twisting of the knee so commonly found in re-injury events.

In including these two additional straps, it is clear to those who would wear such a device that six straps to hold the device to the leg may become confusing and to prevent this, a color coding system has been developed. For each strap, at the insertion or free end a color tab, red, green, blue etc is sewn to the end. At the appropriate corresponding buckle or other searing mechanism the same color is also attached, through sewing or even painting or such means. This allows the wearer of the orthotic to insert the same colored strap into a fastening mechanism with the same color code. This makes the process of placing the brace on the leg much easier.

As generally understood mechanical devices and especially devices involving close contact to each all require lubrication to aid in smooth passage of one component over the other. It is a significant inconvenience for the elderly, the infirm or many others to maintain their orthotic device by lubricating the components to assure proper functionality. If grease or oil is on the mechanical device it may be easily transferred to clothing or the cloth on chairs or the similar. As this device is designed and does allow for all day usage, wherein standard orthosis do not, this is of concern. This invention incorporates the use of a lubricated painting system eliminating the need to use oil or grease on the mechanical components and which eliminates the staining of cloth materials associated with those methods of lubrication.

This invention, to be described herein, provides an orthosis which is designed to match, as closely as possible, the natural motion of the knee, in order that the wearer, may prevent an injury or would be able to proceed as normally as possible after having suffered a partial knee injury. In achieving this natural knee motion this in turn prevents the brace from migrating downwards, eliminating skin irritation, allowing full conformity of the upper and lower cuffs onto the leg and thus fully supporting the leg through its full range of motion without allowing such abnormal motions such as unnecessary backwards or twisting motion of the femur. This allows the knee to be rehabilitated while preventing the potential of further injury. This also accommodates the large displacements seen internally in the knee joint preventing the knee from being forced into abnormal knee motion. This eliminates many of the discomforts normally found when wearing a standard knee orthosis. In combination with this, the invention utilizes a strapping system suitable to prevent the femur from sliding too far backwards, without inhibiting the knee's ability to reach full flexion. The placement of mechanical elements are such so as not to frustrate the process of manufacturing the brace and to better meet the needs of the wearer. Additional features are included with the positional location of the elements and the elements ability to increase the adaptability of the orthosis to the individuals motion requirements and quick recovery.

BRIEF SUMMARY OF THE INVENTION

With the view of satisfying the foregoing problems of traditional orthosis and to better address the complexities of the rehabilitation process, the invention comprises an orthotic device for the purposes of supporting a knee and for the purpose of rehabilitation, while allowing a full range of bending and straightening movements involving sliding, twisting, rotating and lifting of the femur with respect to the tibia. The orthosis has an upper cuff adapted to be secured around a portion of the leg above the knee cap and a lower cuff adapted to be secured around the lower portion of the leg below said knee cap, attachment means on respective upper and lower cuffs adjacent either side of said knee and connecting means connecting said upper cuff and located on the lower cuff and linear bearings means secured to said attachment means on either side of said knee and placed in a position behind said attachment means, said linear bearings means being adapted to permit movement of one said cuff away from the other, rotating with respect to each other and differentially sliding with respect to each other, said orthosis thereby enabling free hinging displacement and a certain degree of tilting and a certain degree of twisting and a certain degree of rotation.

The invention also include a swingable linkage means connected between said upper cuff and said linear bearing means on either side of said orthosis. This swingable linkage is located in front of said linear sliding means for the purpose of allowing said upper cuff and said lower cuff to rotate with respect to one another, without obstructing leg movement or interfering with a second orthosis, on the other knee.

The invention also provides a orthosis wherein said link means comprises a link member, an upper pivot which is attached to said upper cuff and a lower pivot by means of which it connected to said linear bearing means in a manner so as to describe the motion of movement previous stated. Upper pivot and said upper link member having a relationship whereby the center of said sliding member is behind the center of rotation of said upper pivot means.

The invention also provides an orthosis wherein said linear bearing means comprises a slidable rod member of some cross sectional shape, attached to said upper and lower cuffs, and a bearing body being attached to the other of said upper and lower cuffs and the positional relationship of said sliding member to said swingable linkage permitting a rotational movement between said upper cuff to said lower cuff while permitting sliding movements.

This invention also provides an orthosis wherein said linear bearing means comprises a slidable rod member being attached in a fashion so as to allow said link means to be bent to the shape of the individuals leg to allow said link means to continue to function as required and to remain parallel with said link means on the opposite side of said knee.

The invention also provides an orthosis wherein said slidable rod member is attached to said lower cuff and wherein said bearing body is connected to said upper cuff in a position posterior to said swingable linkage member thus allowing an internal and external rotation of the upper cuff to the lower cuff when the knee is fully extended.

The invention also provides a relationship of the sliding linear member behind the center line of the fixed pivot position of the swingable member allowing the sliding member to be of varying cross-section other than round.

The invention also provides a linear bearing for such an orthosis consisting of an elongated sliding rod, which can be fixed to the said lower cuff, and a bearing body having a slide recess extending there through for receiving the slide rod, and in which the bearing body is attached to a portion of the link member connected to an upper cuff. The link member is designed in such a fashion as to allow it to be bent in such a manner, if necessary, to be conformal to the wearers leg and still allow for parallelism with the sliding rod on the other side of the knee.

The invention also provides a link member which consists of an upper plate portion attached to the upper cuff and a link member pivotally secured to the upper and lower link member and gear means secured to said upper and to said lower plate portions and interengaged with one another so as to control relative movement there between.

The invention also provides adjustment means in said linear bearing for adjusting the length of linear movement between said slide rod and said bearing body.

The invention also provides a strapping means attached to said upper cuff and said lower cuff so as to prevent impediment of knee motion and provide additional support to the back of the knee without interfering with bending and straightening of the knee. This strapping system extends from a location on the side most portion of the upper leg to the opposite side most portion of the lower leg on the opposite side, with a suitable adjustment, such as a buckle, for lengthening or shortening accordingly. This strapping means also provides for a strap from the inner most side of the upper leg to the outermost side of the lower leg, with suitable adjustment, thus creating a cross over between the two straps behind the back of the knee.

The invention also provides a strapping means by which a colored tab system is used to identify the strap and the appropriate location of insertion and termination.

The invention also provides a long lasting lubrication means by which the mechanical components do not need on going maintenance with use of greases or oils.

The invention also provides a novel hinge joint mechanism for use in fabricating a knee orthosis. This said mechanism can be attached to the upper cuff and to the lower cuff and allows for the said mechanism to be shaped to the curvature of the wearers leg while allowing full functionality, without compromise, of the orthosis. This said mechanism is manufacturable to the curvature of the wearers leg, by use of tools understood by those skilled in the art of fitting the orthosis, so as not to frustrate their ability to provide the orthosis in a timely fashion. This hinge mechanism can be pre-manufactured prior to assembly with upper and lower cuffs, thus significantly reducing the overall manufacturing process and cost. Part of this reduction in manufacturing time is due to the long lasting lubrication means previously provided, allowing the said mechanical means to be fully finished prior to shaping to the wearers leg and assembly with said upper cuffs and lower cuffs. When the hinge mechanism is shaped to the leg the long lasting lubrication means do not spoil and will adhere to the mechanism with out refinishing after the shaping process thus saving considerable time and cost in the fabrication of the orthosis.

The various features of novelty which characterize the invention are pointed out with more particularly in the claims annexed to and forming part of this disclosure. For a better understanding of this invention, its operating advantages and specific objects attained by its use, reference should be had to the accompanying drawings and descriptive matter in which there are illustrated and described preferred embodiments of the invention.

BRIEF DESCRIPTION OF THE DRAWINGS

FIG. 1 is a perspective illustration in schematic form of a joint orthosis illustrating the invention with the knee in a fully extended position, showing the joint placement of the sliding rod and a schematic form of the diagonal strapping system. Also note tab additions to end of strapping by way of a single example;

FIG. 2 is a side elevation view of the joint orthosis showing the location of the center line of the sliding member being slightly behind the center line of the gear means;

FIG. 3 is a frontal view of the joint orthosis showing the location of the center line of the sliding member being in line with the center of lower linkage means;

FIG. 4 is a schematic in the side view showing the internal bearing surfaces of the sliding member illustrating the use of a spacer to control the length of the travel of the sliding member and illustrating a distance between the centerline of the sliding element and the swingable connections of the hinge element;

FIG. 5 is a front view of same joint orthosis showing the ability to bend the lower links in a fashion suitable to contour closely to the leg without decreasing sliding ability;

DETAILED DESCRIPTION OF THE INVENTION

Figure 6:
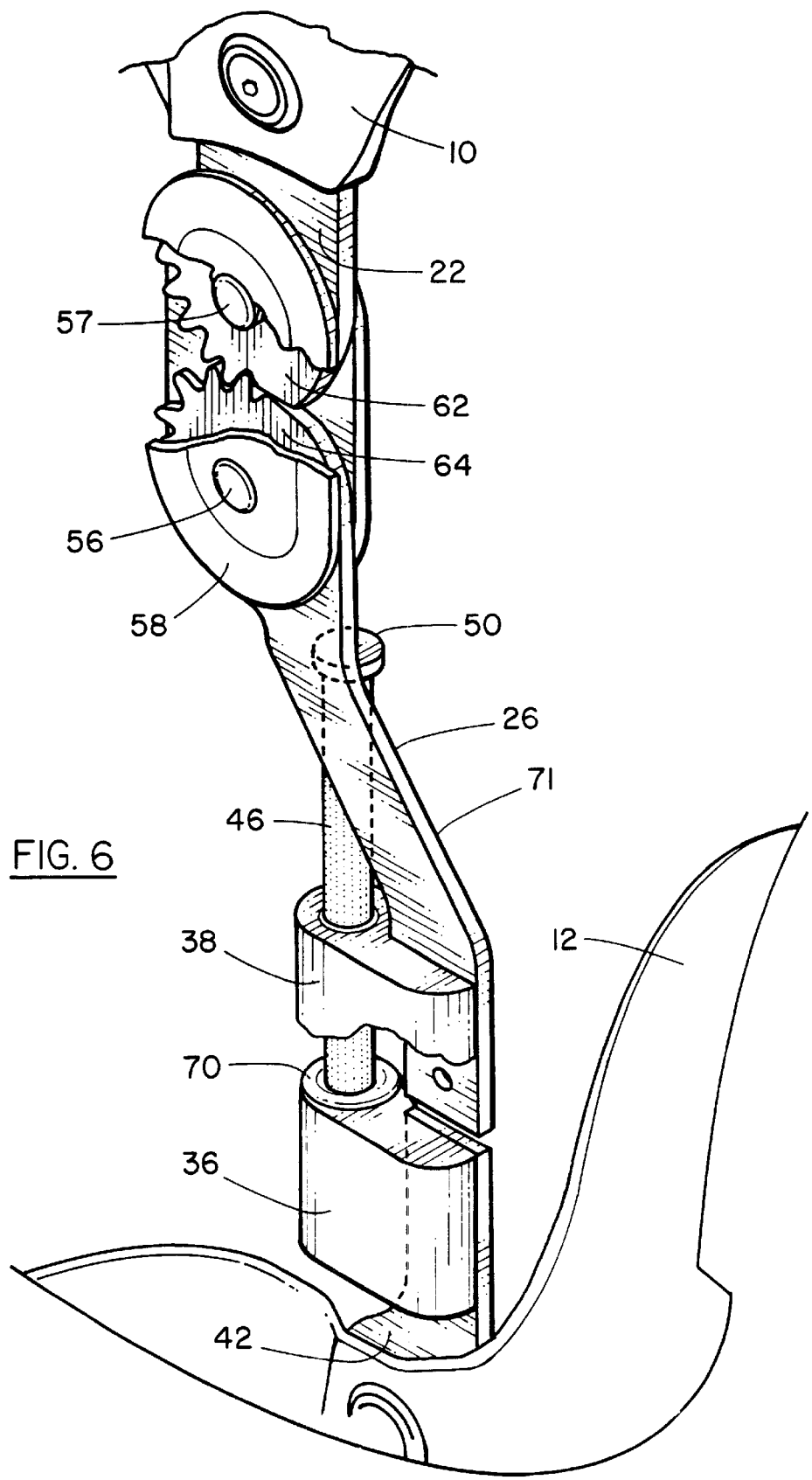
FIG. 6 is an isometric view of the joint orthosis showing inner mechanical components and their interactivity.
Figure 7:
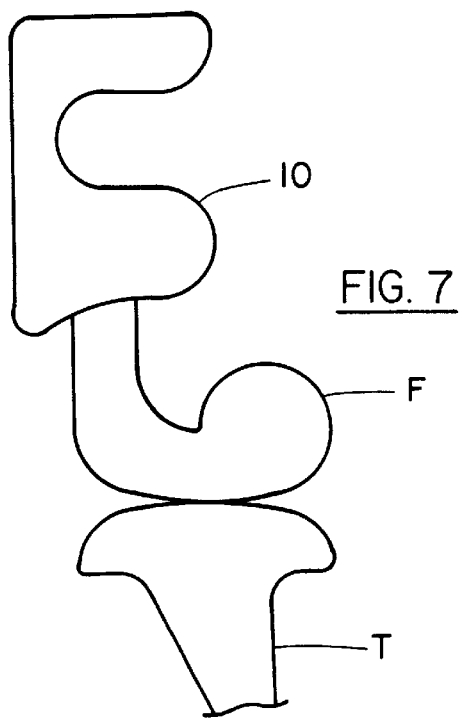
FIGS. 7, 8, 9, 10, illustrates in schematic form, a knee joint consisting of portions of the femur and tibia, and upper cuff from a side elevation to show displacement, sliding and tilt and a frontal view illustrating the different sized knuckles of the femur introducing a rotational motion when the normal knee is flexed.
Figure 8:
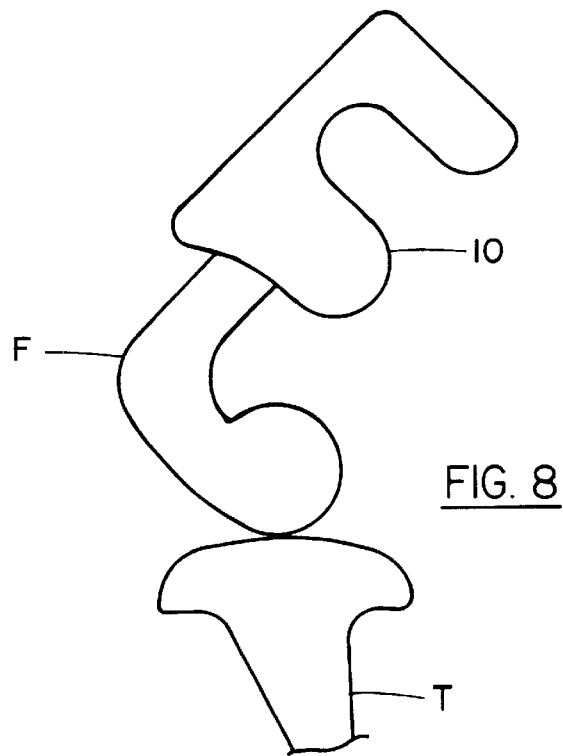
Figure 9:
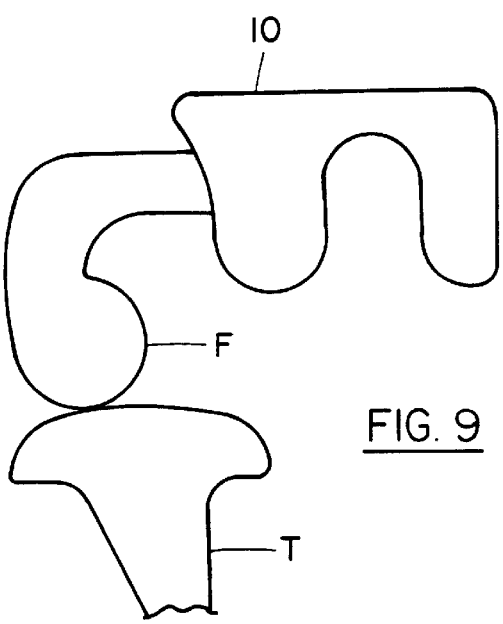

Referring to FIG. 1 the invention is illustrated as a joint orthosis for the knee for the purposes of explaining the invention. It comprises an upper cuff 10 adapted to be strapped around the thigh or upper leg, and a lower cuff 12 adapted to be strapped around the lower leg below the knee. The upper cuff 10 consists of a rigid or semi-rigid or cloth like material having a front and sides, and having one or more straps 16 wich may be wrapped around the thigh and fastened by any suitable means such as buckles, hook and pile fastenings and the like.

The lower cuff 12 consists of a rigid or semi-rigid or cloth like material having a front and sides, and having one or more straps 20 which may be wrapped around the back of the lower leg and be fastened by any suitable means such as buckles, hook and pile fastenings and the like.

The shapes of the upper 10 and lower 12 cuffs are manufactured to conform to the shape of the wearers leg, by any means suitable whether it be digital copying, casting or measuring and scanning of the leg The upper and lower cuffs have hinge means connecting them together in the manner described below.

In order to support the knee the upper and lower cuffs are swingeably connected together on either side of the knee. This is achieved by upper attachment plates 22 and 24 and lower connector plates 26 and 28. Upper attachment plates 22–24 are secured by embedment in the respective sides of the upper cuff 10 and fastened with mechanical fasteners.

Connected with the respective lower connector plates 26–28 are respective linear bearing assemblies indicated generally as outer bearing assembly 30 and inner bearing assembly 32. Reference to inner and outer is with reference to the inside and outside of the leg, simply for the purposes of clarity in explanation and is without limitation. The linear bearing assemblies comprise respective lower mounting blocks 36 and slide bearing bodies 38. The lower mounting blocks 34 are secured to respective lower attachment plates 42–44 by means such as by mechanical fastening or by brazing and/or welding. Plates 42–44 are mounted by embedment in the lower cuffs. The lower mounting blocks 34 support elongated slide rods 46. These rods 46 are illustrated as cylindrical, however they may in fact be square in cross-sectional shape. This would mean a conformal square shape would be seen in the slide bearing bodies 38. The rods 46 terminate at the upper end in caps 50.

The slide bearing bodies 38 are formed with recesses or openings, shaped and dimensioned to receive respective slide rods 46 in accordance with their shape. The slide bodies 38–40 are secured eg. by welding or braising or mechanically fastened to lower connector plates 26–28. The lower connector plates 26–28 may be bent into a pair of generally S-shaped bends, indicated generally as 71 (FIG. 6) in such as manner (FIG. 5.) as to allow sliding bearing bodies to 38 to be located more proximal to the lower leg. The bearing bodies 38 and rods 46 and blocks 34 are thus located offset inwardly relative to the hinge links 58 and 60, and also relative to upper attachment plates 22. This will have the effect of locating the lower ends of the connector plates, and the lower attachment plates, closer to the lower leg, and provide a cleaner more convenient profile and fit.

Lower connector plates 26 and 28 are pivotally connected e.g. by rivets or mechanical fasteners 56, to the lower ends of biaxial link plates 58 and 60. The upper ends of biaxial link plated 58, 60 are pivotally connected by mechanical means 57 to respective upper attachment plates 22 and 24.

In this way the biaxial link plates 58 and 60 can permit rotational movement on two spaced apart parallel axes. In addition, however, in accordance with the invention, the biaxial link plates 58, 60 can also move upwardly and downwardly relative to the lower cuff and lower mounting blocks 34. The lower connector plates 26 and 28 have a centerline 72, is located offset forwardly of slide bearing blocks 38. Blocks 38, and 34 and rod 46 have a centerline 73. The centerline 73 of blocks 34 and 38 and rod 46 thus have a centerline 73 which is offset rearwardly of the centerline of plates 26 by a distance 74 (FIG. 4) to allow rotation lower connector plates 26 and 28, with respect to upper attachment plates 22 and 24.

Upper gear segments 62 are formed on upper attachment orates 22–24 and lower gear segments 64 are formed on lower connector plates 26–28. The gear segments interengage to control hinging action of the link updates 58–60.

Upper straps 16 are attached by means to upper cuff 10 around or across the back of the leg to maintain the position of upper cuff 10 on the leg. The lower straps 20 also attached by means to lower cuff 12 and wrap around or across the back of the leg to maintain the position of lower cuff 12 on the lower portion of said leg. Both the upper straps 16 and the lower straps 20, are, for descriptive purposes, shown to be in a horizontal position relative to the wearer of the orthosis when is standing upright. Unlike these straps, other strapping elements 75 are attached by means to upper cuff 10 from the inside of the upper cuff 10, to the outside of lower cuff 12 by means to adjustment devices such as buckle 76. Strapping elements 77 are attached by means to upper cuff 10 from the outside to the lower cuff on the inside by means such as a buckle 76. These two straps as attached in such a manner, are shown, for descriptive purposes to be in a diagonal position relative to the wearer of the orthosis when in a standing position.

This diagonal strap 75, as with lower horizontal straps 20 and upper horizontal straps 16 have color identification tabs 78, inserted into fastening buckle 76 with associated color identification 80.

By this means when the injured knee bends causing near displacement between the femur and the tibia, the bearing bodies, 38 are able to slide upwardly on the bearing rods 46. Wren the knee bends still further between the femur and the tibia there is also a slight outward tilting motion of the femur relative to the tibia. When this occurs the linear bearing comprising block 38 and rod 46 sliding therein, the rod extending from mounting block 36 on the inside of the knee will be extended still further (i.e. the bearing body 38, will slide further up its rod 46) and the linear bearing on the outside will retract slightly (i.e. the bearing body 38, will slide down its rod 46) thereby accommodating the tilting movement of the knee joint. This has the added effect of allowing he center of the geared segments to remain in the desired location relative to the center of the knee throughout the flexion and extension cycle.

In addition, the location of the sliding bearing bodies centerlines are behind the centerline of the lower gear segment 64. This allows the lower connector plates 26–28 to rotate with respect to the upper attachment plates 22–24 in the horizontal plane. This increases the range of motion of the orthosis, matching it closer to the natural motion of the knee.

It will thus be appreciated that by the use of the invention the knee is able to perform a much greater range of natural movements while still obtaining maximum support from the knee orthosis.

The increase in rotation of the upper cuff assembly relative to the lower cuff assembly, when the knee is in full extension, results from the sliding rod member centerline 73 being located offset some distance 74 from centerline 72 of lower connector plates 26–28. Contributing to this it will also be seen that the knee orthosis is able to provide the range of support without imposing unusual stress on the upper or lower leg. In fact such support is achieved without there being any noticeable tendency for the upper or lower cuff to move relative to the upper or lower leg.

Thus by use of the knee orthosis according to the invention there is improved comfort over a much greater range of movements without causing rubbing friction, skin irritant, or swelling of the leg, as is the case in standard knee orthosis, and without loss of support for the knee joint.

If required the range of movement permitted by the linear bearing can be adjusted, this can be achieved simply by extending, or by retracting the length on one or both of the slide rods 46 out of, or into, their respective mounting blocks 34. This could be achieved in a number of ways, such as threaded adjustment. In this case, it is simply represented by a inserted donut-shaped element 70, located between slide bearing blocks and the lower mounting blocks, which has the same result.

Figure 10:
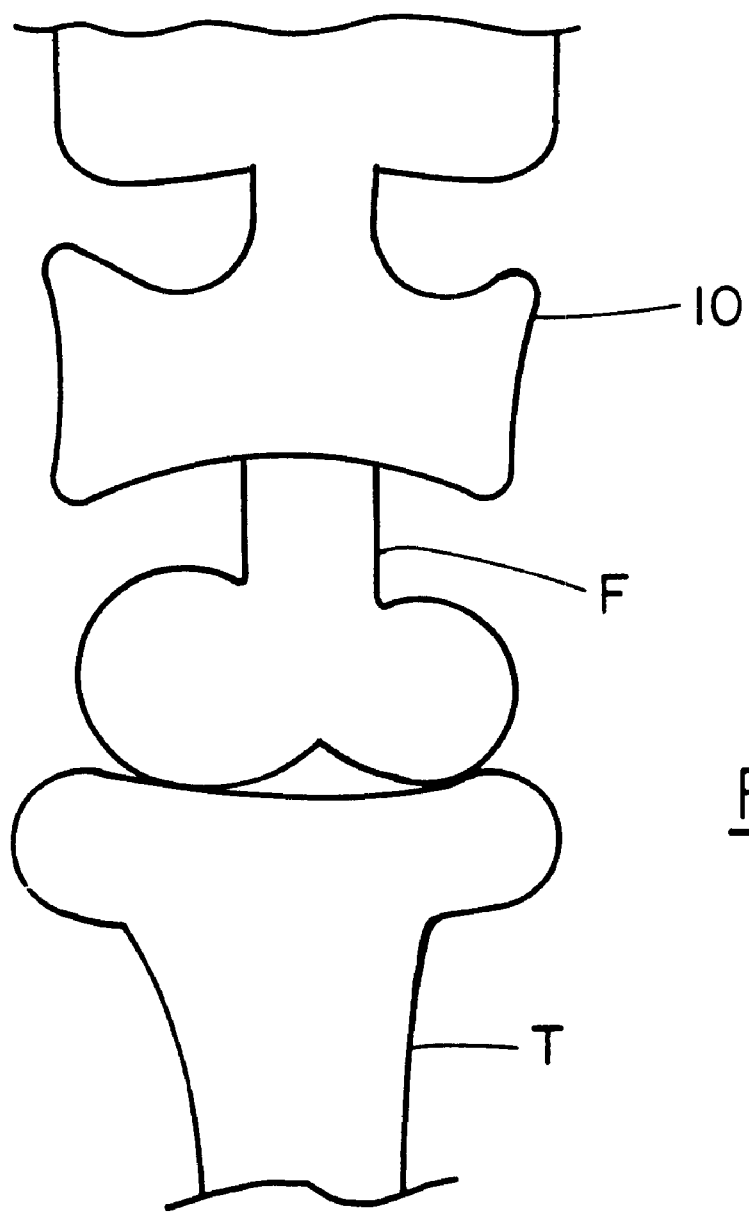

FIGS. 7, 8, 9, 10, represent, in schematic form the movements of the femur and tibia during bending of the knee, The femur is shown as F and the tibia is shown as T. The various of smaller bones that complete the knee are omitted for the sake of clarity, it will be seen that when straight (FIG. 7.) the flatter portion of the femur rests on top of the tibia. As the knee starts to bend, however the femur rolls back on to a reward portion of reduced radius. This causes the femur to be displaced upwardly from the tibia (FIG. 8.) as the knee bends further the femur tilts slightly relative to the tibia (FIG. 10.) this explanation show why the standard knee support cannot provide adequate support for the knee over a full range of movement FIG. 10 shows the tibia and femur from the front and describes the tilting motion and thus the twisting motion as the result of the difference in size of the medial and lateral radiuses knuckles.

The foregoing is a description of a preferred embodiment of the invention which is given by way of an example. The invention is not to be taken as limited to any of the specific features as described but comprehends all such variations there of as come within the scope of the appended claims.

What is claimed is:

1. A knee join orthosis for supporting the tibia and femur while allowing the knee to perform movements involving displacement in sliding, rotating, tilting and lifting of the femur, when in use, comprising:

an upper cuff adapted to be secured around the upper leg above a knee, said upper cuff defining front and side portions;

a lower cuff adapted to be secured around the lower leg below a knee, said lower cuff defining front and side portions;

upper attachment members secured on said upper cuff adjacent to either side of said knee when in use;

lower attachment members connected to said lower cuff adjacent to either side of the knee when in use;

swingable linkage members connected to said upper attachment members on either side of said respective cuff, by first pivotal connection members;

lower connecting members secured to said swingable linkage members by second pivotal members adjacent either side of said knee when in use, and said second pivotal members defining a pivot axis, linear bearing members movably connected between said lower attachment members on said lower cuff on either side of said knee when in use, and said lower connecting members, said linear bearing members being adapted to permit movement of one of said upper and lower cuffs towards and away from the other of said upper and lower cuffs, thereby enabling free movement of said knee when in use both as to displacement and as tilting and twisting and rotation, wherein said linear bearing members define respective bearing axes, and wherein said linear bearing members are located offset rearwardly from said pivot axis of said second pivotal members, and strapping members being attached to said upper cuff and to said lower cuff by which the orthosis can be held to the leg when in use, and wherein said lower connecting member on one side of said orthosis defines a generally S-shaped bend to adapt to the shape of the lower leg when in use while allowing said linear bearing member to function accordingly and with parallelism to said linear bearing member on the opposite side of sad knee when in use.

2. A knee joint orthosis as claimed in claim 1, wherein each of said swingable linkage members comprises two link plates.

3. A knee joint orthosis as claimed in claim 1, wherein each of said linear bearing members each comprise a fixed rod member attached to said lower attachment member, and a bearing body defining a recess therein for sliding reception of said rod member, said bearing body being connected to said swingable link member by said lower connector member.

4. A knee joint orthosis as claimed in claim 3, wherein said bearing body is operably connected by said swingable linkage member to said upper cuff, and is slidable relative to said rod member to permit relative movement between said upper and lower cuff in response to bending movements of said knee when in use.

5. A knee joint orthosis as claimed in claim 4, further comprising a mounting block attached on said lower attachment member, said rod member being mounted on said mounting block, and including an end cap on a free end of said rod member.

6. A knee joint orthosis as claimed in claim 5, wherein said upper attachment member attached to the upper cuff defines a first gear member, and wherein said lower connection member defines a second gear member, said first and second gear members meshing with one another.

7. A knee joint orthosis as claimed in claim 5, further comprising an adjustment member for said linear bearing member for adjusting the length of linear movement available between said rod member and said bearing body.

8. A knee joint orthosis as claimed in claim 3, further comprising permanent lubrication of each of said filed rod members and respective bearing bodies.

9. A knee joint orthosis as claimed in claim 1, wherein said strapping members, by which the orthosis can be held to the leg when in use, prevents the femur from displacing backwards out of the orthosis and holds said upper cuff relative to said lower cuff to prevent torsion between said upper cuff and said lower cuff, while the leg is in the process of bending and straightening.

10. A knee joint orthosis as claimed in claim 1, wherein said strapping members have a portion by which said upper cuff is attached to said lower cuff and including adjustment members for said strapping members.

11. A knee joint orthosis as claimed in claim 1, further comprising strapping members by which said upper cuff is attached to lower cuff and including adjustment members for said strapping members.

12. A knee joint orthosis as claimed in claim 1, wherein said lower connecting member defines an upper portion and a lower portion above and below said S-shaped bend respectively, wherein said upper portion lies generally continuously-planar with said upper attachment member, wherein said lower portion lies generally continuously-planar with said lower attachment member, and wherein said linear bearing member is mounted between said lower portion of said lower connecting member and said lower attachment member, and is offset inwardly towards said lower leg when in use, relative to said upper attachment member.

13. A knee joint orthosis as claimed in claim 1, wherein a said upper attachment member defines a predetermined first plane, wherein a said lower attachment member defines a predetermined second plane, and wherein said second plane is offset inwardly towards said lower leg when in use with respect to said first plane, thereby adapting said orthosis to the shape of said upper leg and said lower leg respectively.

14. A knee joint orthosis for supporting the tibia and femur while allowing the knee to perform movements involving displacement in sliding, rotating, tilting and lifting of the femur, when in use, comprising:

an upper cuff adapted to be secured around the upper leg above a knee, said upper cuff defining front and side portions;

a lower cuff adapted to be secured around the lower leg below a knee, said lower cuff defining front and side portions;

upper attachment members secured on said upper cuff adjacent to either side of said knee when in use;

lower attachment members connected to said lower cuff adjacent to either side of the knee when in use;

swingable linkage members connected to said upper attachment members on either side of said respective cuff, by first pivotal connection members;

lower connecting members secured to said swingable linkage members by second pivotal members adjacent either side of said knee when in use, and said second pivotal members defining a pivot axis, linear bearing members movably connected between said lower attachment members on said lower cuff on either side of said knee when in use, and said lower connecting members, said linear bearing members being adapted to permit movement of one of said upper and lower cuffs towards and away from the other of said upper and lower cuffs, thereby enabling free movement of said knee when in use both as to displacement and as tilting and twisting and rotation, wherein said linear bearing members define respective bearing axes, wherein said linear bearing members are located offset rearwardly from said pivot axis of said second pivotal members, strapping members attached to said upper cuff and to said lower cuff by which the orthosis can be held to the leg when in use, wherein said lower connecting member on one side of said orthosis defines a generally S-shaped bend, wherein said lower connecting member defines an upper portion and a lower portion above and below said S-shaped bend respectively, wherein said upper portion lies generally continuously-planar with said upper attachment member, wherein said lower portion lies generally continuously-planar with said lower attachment member, and wherein said linear bearing member is mounted between said lower portion of said lower connecting member and said lower attachment member, and is offset inwardly towards said lower cuff, relative to said upper attachment member.

* * * * *